(12) United States Patent
Rossi et al.

(10) Patent No.: US 8,506,513 B2
(45) Date of Patent: *Aug. 13, 2013

(54) BLOOD RESERVOIR WITH ULTRASONIC VOLUME SENSOR

(75) Inventors: Ivan Rossi, Poggio Rusco (IT); Ivo Panzani, Mirandola (IT)

(73) Assignee: Sorin Group Italia S.r.l., Milan (IT)

( * ) Notice: Subject to any disclaimer, the term of this patent is extended or adjusted under 35 U.S.C. 154(b) by 136 days.

This patent is subject to a terminal disclaimer.

(21) Appl. No.: 13/085,829

(22) Filed: Apr. 13, 2011

(65) Prior Publication Data

US 2011/0257579 A1      Oct. 20, 2011

Related U.S. Application Data

(63) Continuation-in-part of application No. 12/763,559, filed on Apr. 20, 2010.

(30) Foreign Application Priority Data

Apr. 20, 2010  (EP) .................................... 10160436
Apr. 12, 2011  (EP) .................................... 11162020

(51) Int. Cl.
    *A61M 37/00*      (2006.01)
(52) U.S. Cl.
    USPC ..................... 604/6.15; 604/6.11; 604/6.13
(58) Field of Classification Search
    USPC .................. 604/4.01, 5.01, 6.01, 6.09, 6.14, 604/6.15
    See application file for complete search history.

(56) References Cited

U.S. PATENT DOCUMENTS

| | | |
|---|---|---|
| 3,927,980 A | 12/1975 | Leonard |
| 4,006,745 A | 2/1977 | Sorenson et al. |
| 4,170,765 A | 10/1979 | Austin et al. |
| 4,490,331 A | 12/1984 | Steg, Jr. |
| 4,599,093 A | 7/1986 | Steg, Jr. |
| 4,642,089 A | 2/1987 | Zupkas et al. |
| 4,664,682 A | 5/1987 | Monzen |
| 4,701,101 A | 10/1987 | Sapoff |
| 4,705,497 A | 11/1987 | Shitaokoshi et al. |
| 4,828,543 A | 5/1989 | Weiss et al. |
| 4,846,800 A | 7/1989 | Ouriel et al. |
| 4,876,066 A | 10/1989 | Bringham et al. |

(Continued)

FOREIGN PATENT DOCUMENTS

| | | |
|---|---|---|
| DE | 102005001779 A1 | 9/2006 |
| DE | 102007026010 A1 | 12/2008 |

(Continued)

OTHER PUBLICATIONS

European Search Report issued in EP 10160436, dated Nov. 5, 2010, 9 pages.

(Continued)

*Primary Examiner* — Leslie Deak
(74) *Attorney, Agent, or Firm* — Faegre Baker Daniels LLP

(57) ABSTRACT

A perfusion system that is easy to set-up, use and monitor during a bypass procedure includes at least some disposable components configured to communicate parameters to the perfusion system. An ultrasonic blood level sensor can be used to monitor a blood level or volume within a blood reservoir. The blood level sensor may be utilized in an integrated perfusion system in which the disposable components are configured, as noted above, to communicate with the perfusion system.

18 Claims, 13 Drawing Sheets

(56) References Cited

U.S. PATENT DOCUMENTS

| | | | |
|---|---|---|---|
| 4,955,874 A | 9/1990 | Farrar et al. | |
| 4,991,433 A | 2/1991 | Warnaka et al. | |
| 5,039,430 A | 8/1991 | Corey, Jr. | |
| 5,039,482 A | 8/1991 | Panzani et al. | |
| 5,049,146 A | 9/1991 | Bringham et al. | |
| 5,061,236 A | 10/1991 | Sutherland et al. | |
| 5,078,677 A | 1/1992 | Gentelia et al. | |
| 5,110,549 A | 5/1992 | Gordon | |
| 5,158,533 A | 10/1992 | Strauss et al. | |
| 5,186,431 A | 2/1993 | Tamarim | |
| 5,215,519 A | 6/1993 | Shettigar | |
| 5,226,265 A | 7/1993 | Kelly | |
| 5,270,005 A | 12/1993 | Raible | |
| 5,282,783 A | 2/1994 | Lindsay | |
| 5,303,585 A | 4/1994 | Lichte | |
| 5,304,164 A | 4/1994 | Lindsay | |
| 5,318,510 A | 6/1994 | Cathcart | |
| 5,403,273 A | 4/1995 | Lindsay | |
| 5,411,705 A | 5/1995 | Thor et al. | |
| 5,458,567 A | 10/1995 | Cathcart | |
| 5,458,579 A | 10/1995 | Chodorow et al. | |
| 5,586,085 A * | 12/1996 | Lichte | 367/99 |
| 5,667,485 A | 9/1997 | Lindsay | |
| 5,770,073 A | 6/1998 | Bach et al. | |
| 5,800,721 A | 9/1998 | McBride | |
| 5,955,672 A | 9/1999 | Van Driel et al. | |
| 6,017,493 A * | 1/2000 | Cambron et al. | 422/44 |
| 6,287,270 B1 | 9/2001 | Fini | |
| 6,337,049 B1 | 1/2002 | Tamari | |
| 6,475,176 B2 | 11/2002 | Fini | |
| 6,631,639 B1 | 10/2003 | Dam et al. | |
| 6,652,495 B1 | 11/2003 | Walker | |
| 6,770,048 B2 | 8/2004 | Fini | |
| 7,072,769 B2 | 7/2006 | Fletcher-Haynes et al. | |
| 7,147,614 B2 | 12/2006 | Fini | |
| 7,591,812 B1 * | 9/2009 | Tamari | 604/406 |
| 7,694,570 B1 * | 4/2010 | Dam et al. | 73/644 |
| 2002/0032399 A1 | 3/2002 | Fini | |
| 2003/0144646 A1 | 7/2003 | Se et al. | |
| 2003/0175151 A1 | 9/2003 | Ghelli et al. | |
| 2005/0230313 A1 | 10/2005 | O'Mahony et al. | |
| 2006/0015056 A1 | 1/2006 | Ellingboe et al. | |
| 2009/0012443 A1 | 1/2009 | Ghelli et al. | |
| 2009/0099498 A1 * | 4/2009 | Demers et al. | 604/6.09 |
| 2010/0140182 A1 | 6/2010 | Chapman et al. | |
| 2011/0257578 A1 | 10/2011 | Zanotti et al. | |
| 2012/0130299 A1 | 5/2012 | Knott et al. | |
| 2013/0017119 A1 | 1/2013 | Silvestri et al. | |

FOREIGN PATENT DOCUMENTS

| | | | |
|---|---|---|---|
| EP | 0371173 | A1 | 6/1990 |
| EP | 0472480 | B1 | 2/1992 |
| EP | 0587251 | B1 | 3/1994 |
| EP | 0820775 | B1 | 1/1998 |
| EP | 1053760 | A2 | 11/2000 |
| EP | 1070509 | A2 | 1/2001 |
| EP | 1210956 | B1 | 6/2002 |
| GB | 2009862 | A | 6/1979 |
| GB | 2109934 | A | 6/1983 |
| WO | WO9421311 | A2 | 9/1994 |
| WO | WO9624397 | A2 | 8/1996 |
| WO | WO9733672 | A1 | 9/1997 |
| WO | WO9820957 | A1 | 5/1998 |
| WO | WO9848868 | A1 | 11/1998 |
| WO | WO9908734 | A1 | 2/1999 |
| WO | WO9965413 | A1 | 12/1999 |
| WO | WO0015154 | A1 | 3/2000 |
| WO | WO0044415 | A1 | 8/2000 |
| WO | WO0147442 | A1 | 7/2001 |
| WO | WO0176656 | A2 | 10/2001 |
| WO | WO0239931 | A1 | 5/2002 |
| WO | WO0239933 | A1 | 5/2002 |
| WO | WO02095675 | A1 | 11/2002 |
| WO | WO03026724 | A1 | 4/2003 |
| WO | WO2006021295 | A1 | 2/2006 |
| WO | WO2006057650 | A2 | 7/2006 |
| WO | WO2008119993 | A1 | 10/2008 |

OTHER PUBLICATIONS

European Search Report issued in EP Application No. 11162020, mailed Nov. 7, 2011, 8 pages.

European Search Report issued in EP Application No. 12159592, mailed Apr. 24, 2012, 6 pages.

International Search Report and Written Opinion issued in PCT/IB2011/051639, mailed Nov. 18, 2011, 15 pages.

European Search Report issued in EP Application No. 03004815, completed Apr. 25, 2003, 3 pages.

European Search Report issued in EP Application No. 11173655, completed Nov. 30, 2011, 9 pages.

International Preliminary Report on Patentability, Chapter II, issued in PCT/EP2010/055522, (with translation) mailed May 31, 2011, 13 pages.

International Search Report and Written Opinion issued in PCT/EP2010/055522, (with translation) mailed Aug. 6, 2010, 10 pages.

International Search Report issued in PCT/IB2012/053497, completed Nov. 15, 2012, 4 pages.

\* cited by examiner

BLOOD RESERVOIR WITH ULTRASONIC VOLUME SENSOR

RELATED APPLICATION

This application is a continuation-in-part of U.S. patent application Ser. No. 12/763,559, filed Apr. 20, 2010, entitled "Blood Reservoir with Level Sensor," which is hereby incorporated by reference. This application claims priority to European Application No. 11162020.9, filed Apr. 12, 2011, and to European Application No. 10160436.1, filed Apr. 20, 2010, each of which are hereby incorporated by reference.

TECHNICAL FIELD

The disclosure relates generally to perfusion systems and more particularly to a blood reservoir having a level sensor.

BACKGROUND

Perfusion entails encouraging physiological solutions such as blood through the vessels of the body or a portion of a body of a human or animal. Illustrative examples of situations that may employ perfusion include extracorporeal circulation during cardiopulmonary bypass surgery as well as other surgeries. In some instances, perfusion may be useful in providing extracorporeal circulation during various therapeutic treatments. Perfusion may be useful in maintaining the viability of body parts such as specific organs or limbs, either while the particular body part remains within the body, or while the body part is exterior to the body such as for transplantation or if the body part has been temporarily removed to provide access to other body structures. In some instances, perfusion may be used for a short period of time, typically defined as less than about six hours. In some cases, perfusion may be useful for extended periods of time that are greater than about six hours.

In some instances, blood perfusion systems include one or more pumps in an extracorporeal circuit that is interconnected with the vascular system of a patient. Cardiopulmonary bypass (CPB) surgery typically requires a perfusion system that allows for the temporary cessation of the heart by replacing the function of the heart and lungs. This creates a still operating field and allows for the surgical correction of vascular stenosis, valvular disorders, and congenital heart and great vessel defects. In perfusion systems used for cardiopulmonary bypass surgery, an extracorporeal blood circuit is established that includes at least one pump and an oxygenation device to replace the functions of the heart and lungs.

More specifically, in cardiopulmonary bypass procedures, oxygen-poor blood (i.e., venous blood) is gravity-drained or vacuum suctioned from a large vein entering the heart or other veins (e.g., femoral) in the body and is transferred through a venous line in the extracorporeal circuit. The venous blood is pumped to an oxygenator that provides for oxygen transfer to the blood. Oxygen may be introduced into the blood by transfer across a membrane or, less frequently, by bubbling oxygen through the blood. Concurrently, carbon dioxide is removed across the membrane. The oxygenated blood is then returned through an arterial line to the aorta, femoral, or other main artery.

A perfusion system typically includes various fluid circuitry and components that are configured by medical personnel prior to the bypass procedure. This can be a time consuming process and may require significant manual input of information relating to various components of the system.

SUMMARY

Example 1 is a perfusion system including a heart lung machine and a blood reservoir that is adapted to hold a fluid. The blood reservoir has a volume that is determined by a geometric configuration and may include a communication device for communicating the geometric configuration to the heart lung machine. An ultrasonic blood level sensor is coupled to the blood reservoir and is configured to determine a fluid level within the blood reservoir. A controller is coupled to the heart lung machine and is configured to receive the fluid level and calculate a blood volume contained within the blood reservoir, based on the fluid level and the geometric configuration. The heart lung machine may be configured to adjust an operating parameter based on the calculated blood volume.

In Example 2, the perfusion system of Example 1 in which the ultrasonic blood level sensor includes a spaced apart pair of ultrasonic transducers coupled to a wall of the blood vessel.

In Example 3, the perfusion system of Example 2 in which the pair of ultrasonic transducers includes a first ultrasonic transducer configured to emit a single pulse that generates a flexural wave in the wall and a second ultrasonic transducer configured to receive the flexural wave.

In Example 4, the perfusion system of Example 3 in which the controller is configured to determine the fluid level within the blood reservoir based on phase delays in the flexural wave.

In Example 5, the perfusion system of Example 1 in which the ultrasonic blood level sensor includes a piezoelectric element disposed within a housing.

In Example 6, the perfusion system of Example 5 in which the ultrasonic blood level sensor is removably secured to the blood reservoir.

In Example 7, the perfusion system of Example 6 in which the ultrasonic blood level sensor may be adhesively secured to the blood reservoir.

In Example 8, the perfusion system of Example 7 in which the ultrasonic further includes double faced tape, with one adhesive side secured to the housing and an opposing adhesive side secured to the blood reservoir.

In Example 9, the perfusion system of any of Examples 1-8 in which the ultrasonic sensor is molded into a wall of the blood reservoir.

In Example 10, the perfusion system of any of Examples 1-9 in which the controller is further configured to operate the heart lung machine in accordance with the calculated blood volume in the blood reservoir.

In Example 11, the perfusion system of Example 1, further including a polymeric tube disposed within the blood reservoir, with the ultrasonic blood level sensor disposed proximate an upper end of the polymeric tube.

Example 12 is a blood reservoir system including a blood reservoir that includes a wall and that is configured to hold a blood volume. An ultrasonic blood level sensor is securable to the blood reservoir and is configured to provide an electrical signal indicative to a level of blood within the blood reservoir. A controller is configured to receive the electrical signal from the ultrasonic blood level sensor and output a signal indicative of a blood volume within the blood reservoir.

In Example 13, the blood reservoir system of Example 12 in which the ultrasonic sensor is structurally integrated into the blood reservoir.

In Example 14, the blood reservoir system of Example 12 in which the ultrasonic sensor is integrated into a cover portion of the blood reservoir.

In Example 15, the blood reservoir system of any of Examples 12-14, in which the ultrasonic sensor is structurally separate from the blood reservoir and further wherein the ultrasonic sensor is configured for removably coupling with the blood reservoir.

In Example 16, the blood reservoir system of any of Examples 12-15 further comprising a guide tube disposed within the blood reservoir and coupled to a top surface of the reservoir and further wherein the ultrasonic sensor is secured to the reservoir such that the sensor is in communication with an interior lumen of the guide tube.

In Example 17, the blood reservoir system of any of Examples 12-16, in which the blood reservoir comprises a soft shell reservoir.

In Example 18, the blood reservoir system of any of Examples 12-17, wherein the blood reservoir comprises a hard shell reservoir.

In Example 19, the blood reservoir system of any of Examples 12-18, in which the ultrasonic sensor is configured to communicate wirelessly with the controller.

In Example 20, the blood reservoir system of Example 15, in which the ultrasonic sensor includes an active RFID tag that communicates with an RF sensor operably connected to the controller.

While various embodiments are shown and described herein with reference to a blood level sensor, many of these embodiments may also be described with reference to a blood volume sensor. As described in further detail below, where the geometry of the blood reservoir is known, it is possible to provide information from the sensor as either a level or a volume, as the volume of fluid in the reservoir may be readily calculated from the detected or sensed blood level, based on the known geometry of the reservoir.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

The disclosure relates to a perfusion system that is easy to set-up, use and monitor during a bypass procedure. In some embodiments, the disclosure relates to a perfusion system in which at least some of the disposable components used with the perfusion system are encoded with set-up and/or operational parameters. In some embodiments, the disclosure relates to a blood sensor that can be used to monitor a blood level or volume within a blood reservoir. The blood sensor may be utilized in an integrated perfusion system in which the disposable components are configured, as noted above, to communicate with the perfusion system. In some embodiments, the blood sensor may be utilized with a perfusion system lacking communication with disposables. According to various embodiments, the blood sensor may be considered as either a blood level sensor or a blood volume sensor, as the blood volume is readily ascertainable from the sensed blood level, based on the known geometric configuration of the blood reservoir.

Figure 1:
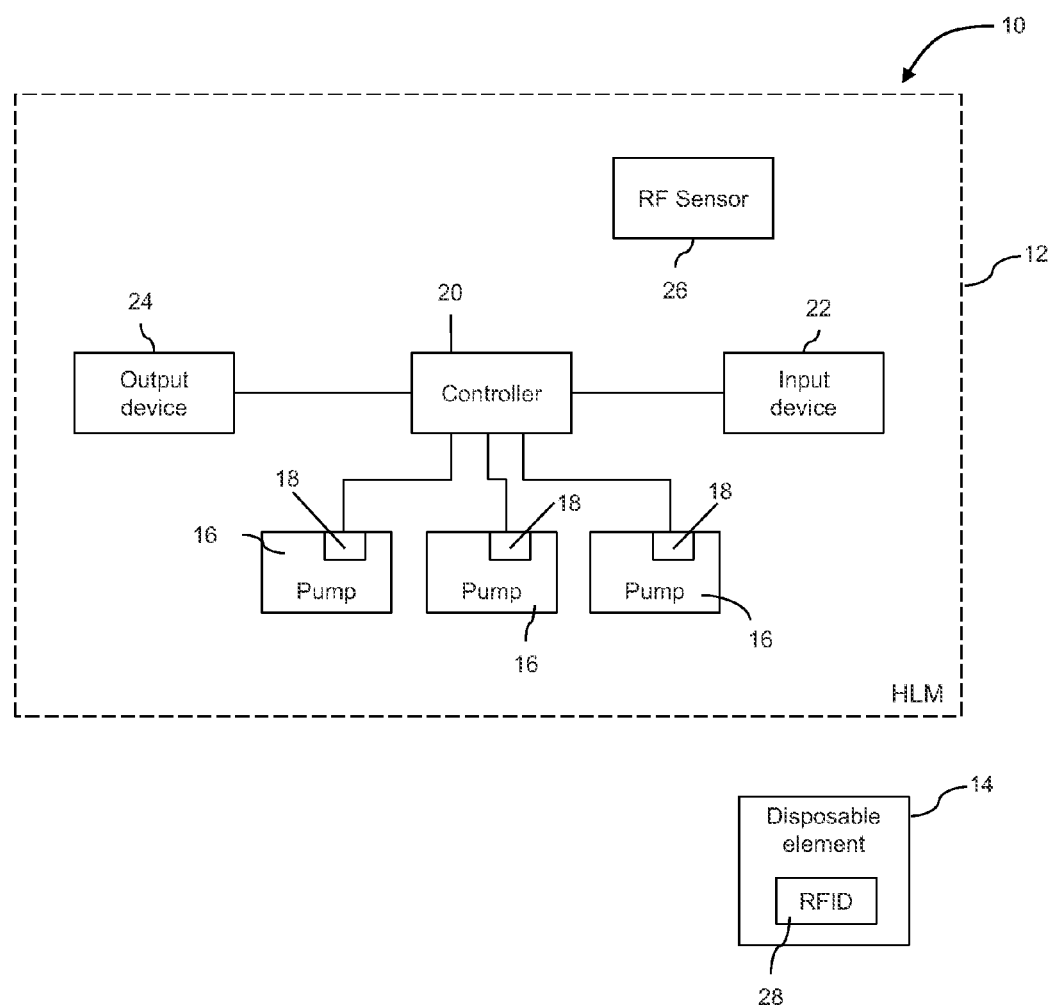
FIG. 1 is a schematic illustration of an integrated perfusion system in accordance with an embodiment of the invention.

FIG. 1 is a schematic illustration of an integrated perfusion system 10 including a heart lung machine (HLM) 12 and a disposable element 14. While only a single disposable element 14 is shown for ease of illustration, in many embodiments a plurality of different disposable elements 14 may be utilized in combination with the HLM 12. Each of the HLM 12 and the disposable element 14 will be described in greater detail subsequently. The HLM 12 includes a number of different components. It is to be understood that the particular components illustrated herein as being part of the HLM 12 is merely an example, as the HLM 12 may include other components or different numbers of components.

In the illustrated embodiment, the HLM 12 includes three pump modules 16, but may include as few as two pump modules 16 or as many as six or seven pump modules 16. In some embodiments, the pump modules 16 may be roller or peristaltic pumps. In some embodiments, one or more of the pump modules 16 may be centrifugal pumps. Each of the pump modules 16 may be used to provide fluid or gas for delivery to or removal from the heart chambers and/or surgical field. In an illustrative but non-limiting example, one pump module 16 draws blood from the heart, another provides surgical suction and a third provides cardioplegia fluid (high potassium solution to arrest the heart). Additional pump modules 16 (not shown) may be added to provide additional fluid transfer.

Each pump module 16 includes a control unit 18. In some embodiments, each control unit 18 may be configured to operate and monitor the operation of the particular pump module 16 to which it is attached or otherwise connected to. In some embodiments, each control unit 18 may include one or more input devices (not illustrated) such as switches, knobs, buttons, touch screens and the like so that the perfusionist may adjust the operation of the particular pump module 16. Each pump module 16 may include an alphanumeric display that the control unit 18 can use to display, for example, the value of a setting, the value of a current operating parameter, confirmation that the pump module 16 is operating normally, and the like.

The HLM 12 includes a controller 20 that is in communication with the control units 18 and that is configured to operate the HLM 12. In some embodiments, the controller 20 is configured to monitor one or more sensors that may be distributed on the HLM 12 and/or within the disposable element 14 to monitor operation of the HLM 12. Examples of such sensors (not illustrated for ease of illustration) include but are not limited to flow meters, pressure sensors, temperature sensors, blood gas analyzers and the like.

While the control units 18 and the controller 20 are illustrated as distinct elements, in some embodiments it is contemplated that these elements may be combined in a single controller. In some embodiments, it is contemplated that the control units 18, in combination, may be configured to operate the HLM 12, thereby negating a need for the controller 20.

The controller 20 communicates with an input device 22 and an output device 24. The input device 22 may be used by the perfusionist to enter information that is not otherwise entered into the control units 18. The output device 24 may be used by the HLM 12 to display pertinent information to the perfusionist. In some embodiments, the input device 22 may be a key pad, a keyboard, a touch screen, and the like. In some embodiments, the output device 24 may be a monitor. In some embodiments, either of the input device 22 and/or the output device 24 may be a computer such as a personal computer, a laptop computer, a notebook computer or a tablet computer. In some cases, the input device 22 and the output device 24 may be manifested in a single computer.

According to various embodiments, the HLM 12 also includes an RF sensor 26. In some embodiments, the RF sensor 26 may be configured to receive information from an active RFID tag placed on the disposable element 14. In some embodiments, the RF sensor 26 may be a hand held device that is used to scan a passive RFID tag on the disposable element 14. According to other embodiments, the RF sensor 26 is replaced with any of a variety of known wireless communication receivers. The disposable element 14 includes an RFID tag 28. According to various embodiments, the disposable element 14 includes either an active RFID tag or a passive RFID tag (or both) configured to communicate with the RF sensor 26. In other embodiments, the RFID tag 28 is replaced with any of a variety of known wireless communication transmitters. According to various embodiments, the system includes one or more of the RFID configurations disclosed in U.S. patent application Ser. No. 12/763,561, filed on Apr. 20, 2010, which is hereby incorporated by reference in its entirety.

Passive RFID tags lack a power supply, and instead are powered by an induced current caused by an incoming radio-frequency scan. Because there is no onboard power supply, a passive RFID tag is smaller and less expensive. An active RFID tag includes an onboard power supply such as a battery. While this increases the size and expense of the RFID tag, an advantage is that the RFID tag can store more information and can transmit further. RFID tags, whether active or passive, may be selected to transmit at a variety of frequencies depending on need. Options include low frequency (about 100 to 500 kilohertz), high frequency (about 10 to 15 megahertz), ultra high frequency (about 860 to 960 megahertz) and microwave (about 2.45 gigahertz).

As noted above, the disposable element 14 may be considered as generically representing one, two or a plurality of different disposable elements that may be used in conjunction with the HLM 12. Illustrative but non-limiting examples of disposable elements 14 include tubing sets, blood reservoirs, oxygenators, heat exchangers and arterial filters. In some embodiments, a tubing set includes a number of different tubes, potentially of different lengths and sizes, for providing fluid flow between components of the HLM 12 as well as providing fluid flow between the HLM 12 and a patient.

In some embodiments, the disposable element 14 may be a blood reservoir such as a venous blood reservoir, a vent blood reservoir, a cardiotomy or suction blood reservoir. In some embodiments, the disposable element 14 may be a blood reservoir that combines one or more of a venous blood reservoir, a vent reservoir and/or a suction reservoir in a single structure. In some embodiments, one or more of the aforementioned sensors may be disposable elements that include an RFID tag 28 either to provide information identifying the sensor or even for transmitting sensed values to the controller 20.

The RFID tag 28 may be attached to the disposable element 14 in any appropriate manner. In some embodiments, the RFID tag 28 may be adhesively secured to the disposable element 14. In some embodiments, the RFID tag 28 may be molded into the disposable element 14. In some embodiments the RFID tag 28 may be a stand alone card, similar in size and shape to a credit card, that may simply be packed with the disposable element 14 in such a way that it can be removed by the user and swiped by the RF sensor 26. However the RFID tag 28 is attached, the RFID tag 28 may be programmed with or otherwise configured to include a wide variety of information pertaining to the disposable element 14.

In some embodiments, the RFID tag 28 may include data or identifying information for the disposable element 14. Illustrative but non-limiting examples of identifying information include the name of the particular disposable element 14, a reference code, a serial number, a lot number, an expiration date and the like. In some embodiments, this information may be communicated to the controller 20 and may, for example, be used by the controller 20 to confirm that the proper disposable elements 14 are being used for a particular setting, patient or the like. As an example, the controller 20 may recognize that a pediatric tubing set is being used in combination with an adult-sized blood reservoir or other component. As another example, the controller 20 may recognize that an expected component is missing. There are a variety of other potential mismatches in equipment that may be recognized by the controller 20 as a result of the information provided by the RFID tag 28 attached to each of the one or more disposable elements 14.

In some embodiments, the RFID tag 28 may include descriptive or design information for the disposable element 14. Illustrative but non-limiting examples of descriptive or design information include specific materials, a list of components, priming volume of a component or tubing circuit, tubing size, tubing length, minimum and maximum working pressures, minimum and maximum working volume, and the like. In some embodiments, this information may be communicated to the controller 20 and may be used by the controller 20 to at least partially configure and/or operate the HLM 12. As an example, the controller 20 may use the sizing information provided from each of the disposable elements 14 to determine a working blood volume for the HLM 12.

In some embodiments, the information obtained from the RFID tag 28 may also be provided to the perfusionist. In some embodiments, the output device 24 may be configured to provide alphanumeric or graphical representations of the obtained information. In some cases, the RFID tag 28 may include instructional information that may be displayed by the output device 24 in order to instruct the perfusionist in optimal setup and/or operation of a particular disposable element 14. In various embodiments, the output device 24 may be a computer such as a personal computer, a laptop computer, a notebook computer or a tablet computer. In some embodiments, the RFID tag 28 may include displayable information that, for example, suggests an optimal circuit design based upon the specific components being used, or perhaps updated use instructions. In some embodiments, information from the RFID tag 28 is displayed on an integrated data management system (DMS).

In some embodiments, the RFID tag 28 may include information that a manufacturer of the disposable element 14 wants to provide to the user. Examples of such information may include technical features of the disposable element 14 that have changed from a previous version or even a previous batch. Another example includes information that can be displayed by the output device 24 that require the user to acknowledge receipt of the information before the controller 20 proceeds with a particular procedure. In some cases, the RFID tag 28 may receive error messages from the controller 20, and the RFID tag 28 may then be returned to the manufacturer, thereby providing the manufacturer with feedback regarding the performance of the disposable element 14 as well as other components.

Figure 2:
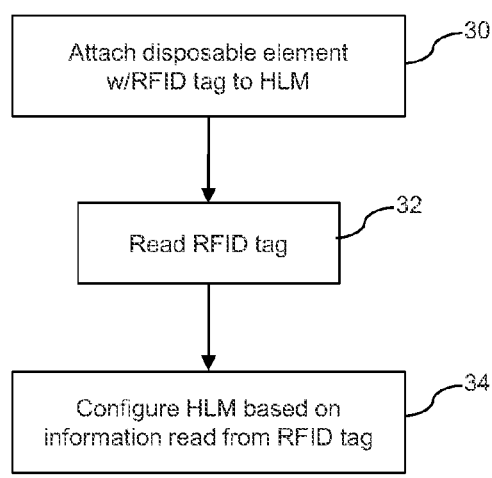
FIG. 2 is a flow diagram illustrating a method that can be carried out by the integrated perfusion system of FIG. 1.

FIG. 2 is a flow diagram illustrating a method that may be carried out using the perfusion system 10 of FIG. 1. A disposable element 14 having an RFID tag 28 may be attached to the HLM 12, as generally shown at block 30. At block 32, the RFID tag 28 is read. As noted above, the RFID tag 28 may be an active RFID tag or a passive RFID tag. In some embodiments, the RFID tag 28 may be read before the disposable element 14 is attached to the HLM 12. In some embodiments, the RFID tag 28 may be read after attachment. At block 34, the HLM 12 is configured based at least in part upon information that was read from the RFID tag 28 at block 32. In some embodiments, the controller 20 automatically configures the HLM 12 in response to this information.

Figure 3:
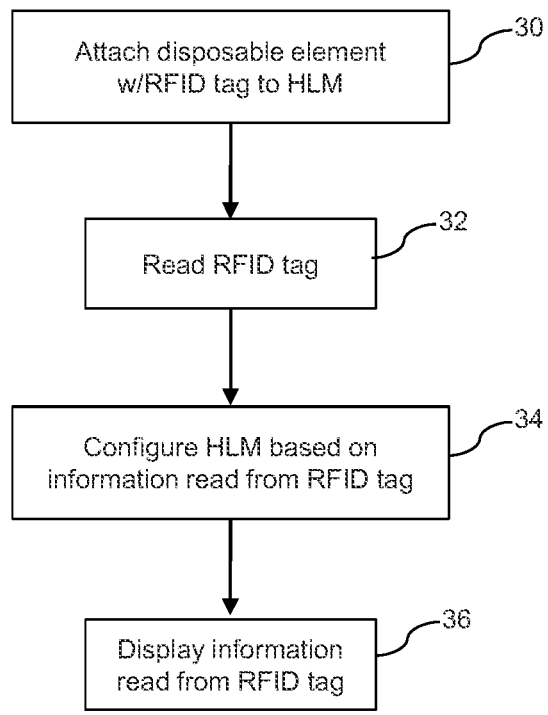
FIG. 3 is a flow diagram illustrating a method that can be carried out by the integrated perfusion system of FIG. 1.

FIG. 3 is a flow diagram illustrating a method that may be carried out using the perfusion system 10 of FIG. 1. A disposable element 14 having an RFID tag 28 may be attached to the HLM 12, as generally shown at block 30. At block 32, the RFID tag 28 is read. The RFID tag 28 may be read either before or after the disposable element 14 is attached to the HLM 12. At block 34, the HLM 12 is configured based at least in part upon information that was read from the RFID tag 28 at block 32. In some embodiments, the controller 20 automatically configures the HLM 12 in response to this information. At least some of the information read from the RFID tag 28 may be displayed on the output device 24, as seen at block 36.

Figure 4:
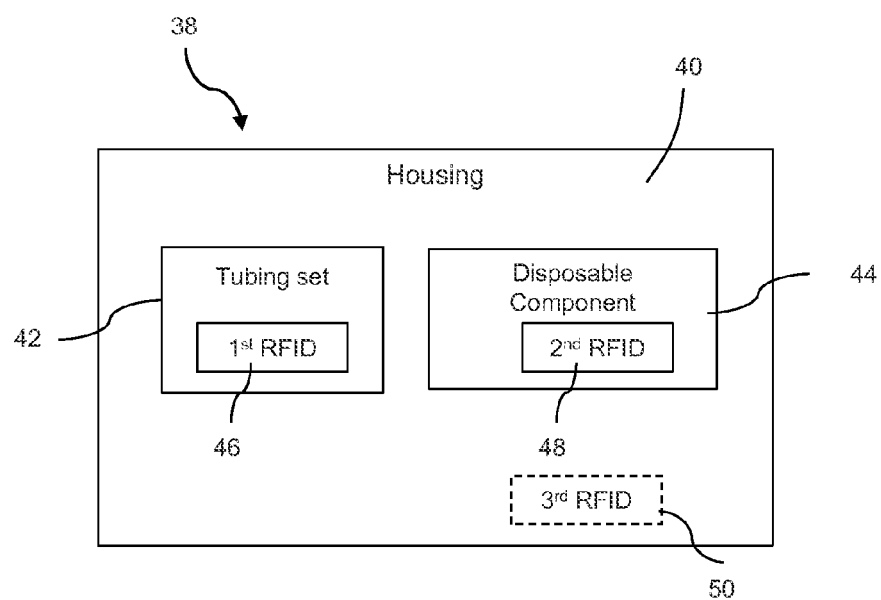
FIG. 4 is a schematic illustration of a heart lung machine pack that may be utilized with the integrated perfusion system of FIG. 1.

FIG. 4 is a schematic illustration of a heart lung machine pack 38 that may be utilized with the perfusion system 10 of FIG. 1. In some embodiments, the heart lung machine pack 38 may include all of the disposable elements 14 that will be used together for a particular patient and may be customized for the particular patient. In some embodiments, the heart lung machine pack 38 may include a housing 40 that, once filled, can be sealed up to keep the contents clean and sterile.

In the illustrated embodiment, the heart lung machine pack 38 includes a tubing set 42 and a disposable component 44. The tubing set 42 may include a plurality of different tubes. The disposable component 44 may be any of the disposable components discussed above with respect to the disposable element 14. In some embodiments, the heart lung machine pack 38 will include a plurality of different disposable components 44. The tubing set 42 includes a first RFID tag 46 while the disposable component 44 includes a second RFID tag 48. As discussed above, each of the first RFID tag 46 and the second RFID tag 48 may be either active or passive RFID tags and may include readable information pertaining to the component to which they are attached. In some instances, the housing 40 may include a third RFID tag 50 that, for example, identifies the contents of the heart lung machine pack 38. In some embodiments, the first RFID tag 46 and the second RFID tag 48 may not be included, as the third RFID tag 50 may be encoded with all of the information for the tubing set 42 and the disposable component 44.

Figure 5:
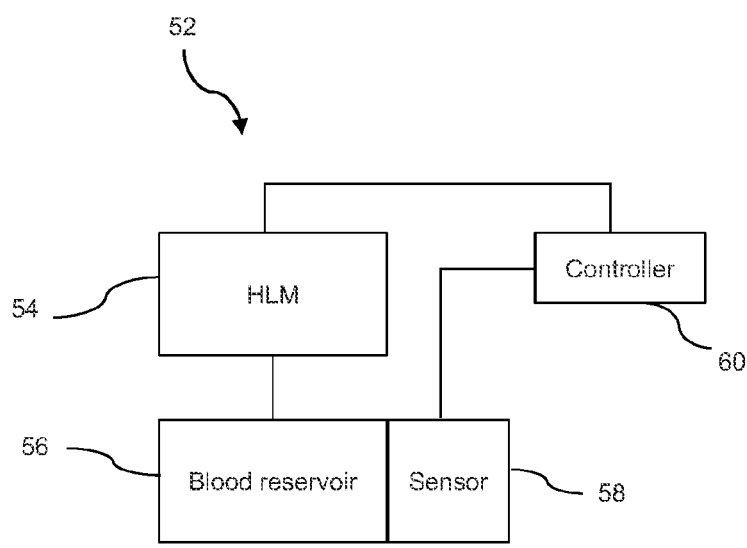
FIG. 5 is a schematic illustration of a perfusion system in accordance with an embodiment of the invention.

FIG. 5 is a schematic illustration of a perfusion system 52. The perfusion system 52 includes an HLM 54 that in some embodiments may be similar in structure and operation to the HLM 12 discussed with respect to FIG. 1. The perfusion system 52 also includes a blood reservoir 56, a blood level/volume sensor 58 and a controller 60. The blood reservoir 56 may be a venous blood reservoir, a vent blood reservoir, a cardiotomy or suction blood reservoir. In some embodiments, the blood reservoir 56 may be a blood reservoir that combines one or more of a venous blood reservoir, a vent reservoir and/or a suction reservoir in a single structure.

The blood volume sensor 58 may be configured to continuously monitor a variable blood level within the blood reservoir 56. The blood volume sensor may be chosen from a variety of different sensing technologies. In some embodiments, as will be discussed subsequently with respect to FIGS. 12-16, the sensor 58 may be an ultrasonic sensor in which ultrasound is used to detect the blood level within the blood reservoir 56. In some embodiments, the sensor 58 may be an optical sensor in which a laser beam or light from an infrared light source is reflected by the liquid-air interface and the reflected light beam is detected by the sensor 58. In some embodiments, the blood level/volume sensor 58 is an optical distance sensor of the type commercially sold by Leuze electronic GmbH located in Owen/Teck, Germany (e.g., ODSL8, ODSL 30, or ODS 96). In some embodiments, the sensor 58 may be a load cell or scale that is configured to measure a mass of the blood reservoir 56 and thereby determine the volume of blood therein.

In some embodiments, the blood volume sensor 58 may be a capacitive sensor (better illustrated in subsequent Figures) that outputs an electrical signal that is proportional to or otherwise related to a blood level and/or volume within the blood reservoir 56. The electrical signal may be communicated in either a wired or wireless fashion to the controller 60. While the controller 60 is shown as a distinct element, in some embodiments the controller 60 is manifested as part of a controller (similar to the controller 20) operating the HLM 54.

In some embodiments, the blood volume sensor 58 may be modeled after capacitive sensors (e.g., CLC or CLW series) available commercially from Sensortechnics GmbH located in Puchheim, Germany, which are configured to provide contact-free measurement of continuous liquid level. The sensor available from Sensortechnics may be disposed on an outer surface of a container and provides an electrical signal representative of the liquid level within the container. In some instances, the Sensortechnics sensor may be spaced as much as about five millimeters from the liquid within the sensor, with no more than about twenty percent air gap between the sensor and the liquid. According to various embodiments, the capacitive sensor 58 is molded inside the blood reservoir 56, such that only the connector is accessible outside the reservoir. In these embodiments, the sensor 58 is protected by the plastic material of the blood reservoir.

In some embodiments, the sensor may undergo an initial configuration to adapt the sensor to the particulars of the container itself as well as the liquid within the container. In some embodiments, the blood volume sensor 58 has a five pin electrical connection, including a voltage source, an analog signal out, a digital signal out, a teach-in pin and a ground. In some embodiments, the sensor 58 is a capacitive sensor such as the Balluff SmartLevel sensor commercially sold by Balluff GmbH located in Neuhausen, Germany.

The controller 60 may receive an electrical signal that is proportional to or at least related to a blood level within the blood reservoir 56. The controller 60 may calculate a blood volume based on this electrical signal as well as a known shape or geometry of the blood reservoir 56. In some embodiments, the blood reservoir 56 may include an RFID tag (not illustrated) that provides the controller 60 with information pertaining to the known geometry of the blood reservoir 56. According to various exemplary embodiments, the volume of the blood reservoir is calculated according to one or more of the techniques described in copending U.S. patent application Ser. No. 12/763,561, filed on Apr. 20, 2010, which is hereby incorporated by reference. According to various embodiments, the volume of the blood reservoir is calculated by integrating the detected level of blood in the reservoir against the known cross-sectional area of the blood reservoir at various heights throughout the reservoir.

If the blood reservoir 56 is a hard shell blood reservoir, the known geometry of the blood reservoir 56 may include the cross-sectional area of the blood reservoir 56, or a width and depth of the blood reservoir 56 as well as details on how this cross-sectional area varies relative to height within the blood reservoir 56. If the blood reservoir 56 is a soft shell reservoir, the known geometry may be based at least in part upon a known lateral expansion rate of the soft shell reservoir relative to the blood level within the blood reservoir 56.

Figure 6:
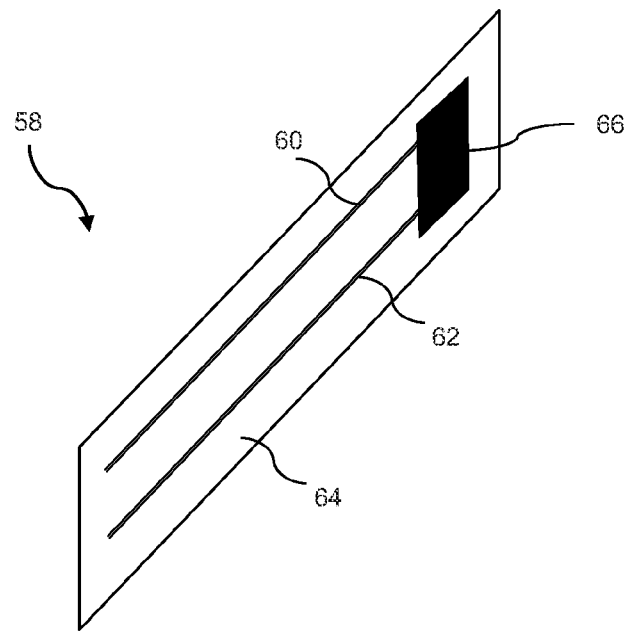
FIG. 6 is an illustration of a blood level sensor that may be utilized with the perfusion system of FIG. 5.

As can be seen in FIG. 6, the blood volume sensor 58 includes a first elongate electrode 60 and a second elongate electrode 62. The first elongate electrode 60 and the second elongate electrode 62 are disposed along a flexible substrate 64. In some embodiments, the flexible substrate 64 may include an adhesive layer that can be used to secure the sensor 58 to the blood reservoir 56. A connector socket 66 is secured to the flexible substrate 64 and is electrically connected to the first elongate electrode 60 and the second elongate electrode 62 in order to permit an electrical connection between the first and second electrodes 60, 62 and an electrical cable (not illustrated in this Figure). In some embodiments, rather than an elongate sensor, the sensor 58 may include two or more distinct SMARTLEVEL™ capacitive sensors such as those available commercially from Balluff. These sensors may provide a binary, yes/no signal. By locating several of these sensors at differing levels proximate the blood reservoir 56, the blood level and/or volume within the blood reservoir 56 may be determined.

Figure 7:
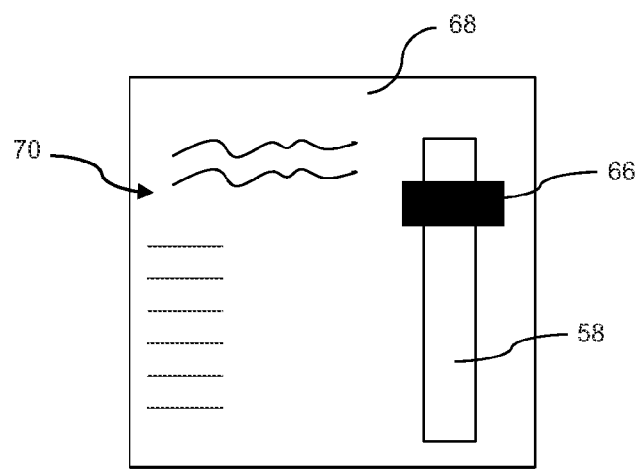
FIG. 7 is an illustration of a blood level sensor incorporated into a label that may be utilized with the perfusion system of FIG. 5.

In some embodiments, the sensor 58 may be attached to or otherwise integrated into a label 68 as seen in FIG. 7. The label 68 may include various indicia 70 such as use instructions, volume indicators and the like. In some embodiments, the label 68 may include an adhesive side for attachment to an outer surface of the blood reservoir 56. In some embodiments, the label 68 is oriented on the blood reservoir such that a lower portion of the sensor 58 is aligned at or near a bottom of the blood reservoir 56.

Figure 8:
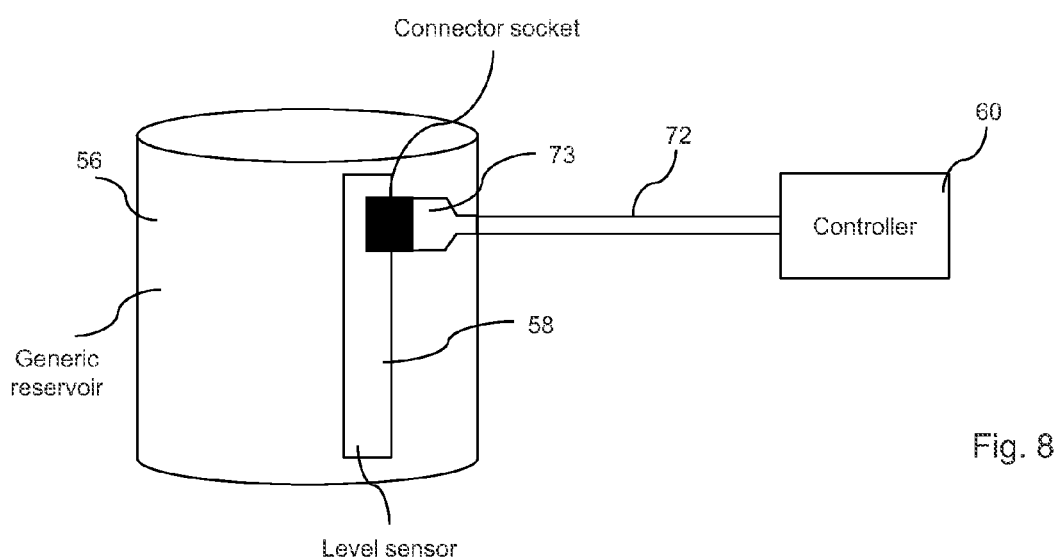
FIG. 8 is an illustration of a blood reservoir including a blood level sensor in accordance with an embodiment of the invention.

FIG. 8 is an illustration of the blood volume sensor 58 attached to the blood reservoir 56. An electrical cable 72 provides an electrical connection between the sensor 58 and the controller 60. The electrical cable 72 includes a plug 73 that is configured to connect to the electrical connector 66. In some embodiments, the plug 73 includes circuitry that converts a detected capacitance into a voltage signal that the controller 60 can use to calculate the blood volume. In some embodiments, the plug 73 further includes circuitry to calculate the blood volume.

Figure 9:
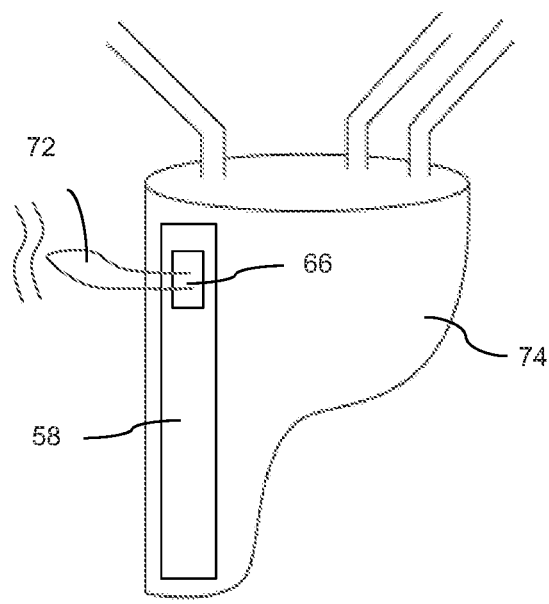
FIG. 9 is an illustration of a hard shell blood reservoir including a blood level sensor in accordance with an embodiment of the invention.
Figure 10:
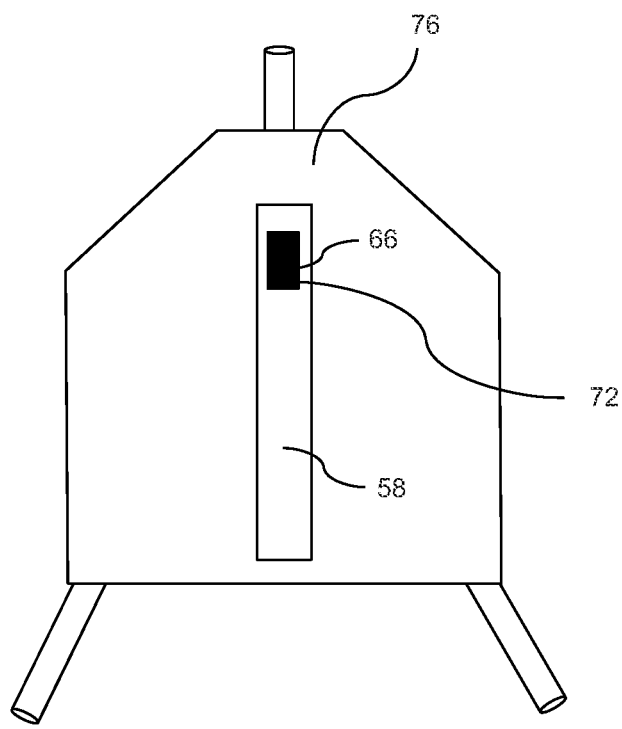
FIG. 10 is an illustration of a soft shell blood reservoir including a blood level sensor in accordance with an embodiment of the invention.

As noted above, the blood reservoir 56 may be either a hard shell reservoir or a soft shell reservoir. FIG. 9 illustrates a hard shell reservoir 74 bearing the blood volume sensor 58 while FIG. 10 illustrates a soft shell reservoir 76 including the sensor 58. In either case, the reservoir may be constructed to include the sensor 58. In some embodiments, the blood level sensor 58 may be adhesively secured to an existing blood reservoir.

Figure 11:
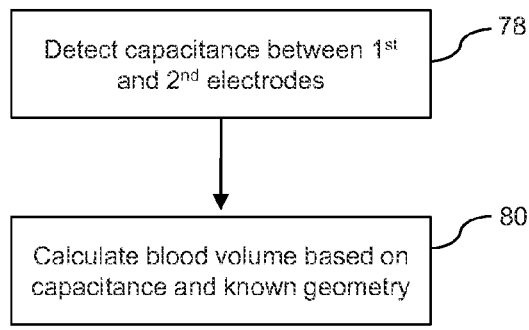
FIG. 11 is a flow diagram illustrating a method that can be carried out using the perfusion system of FIG. 5.

FIG. 11 is a flow diagram illustrating a method that may be carried out using the perfusion system 52 of FIG. 5. A capacitance between first and second electrodes may be detected, as referenced at block 78. In some embodiments, as discussed above, the capacitance may be converted into an electrical signal representing the blood level by circuitry within the plug 73. In embodiments using the CLC series Sensortechnics sensor, for example, the sensor will output a voltage between 0.5 and 4.5 volts. Assuming the sensor pad is appropriately located on the reservoir, this voltage indicates a level or height of the liquid in the reservoir. At block 80, the controller 60 may calculate a blood volume that is based upon the detected capacitance and a known dimensions or geometry of the blood reservoir 56. In some embodiments, the controller 60 (or other circuitry within the HLM 54) may provide the circuitry in the plug 73 with sufficient information (e.g., dimensions or geometry) regarding the blood reservoir 56 to permit the circuitry to perform the blood volume calculation. In some embodiments, the calculated blood volume is communicated to the HLM 54 so that it may adjust an operating parameter of the HLM 54. In various exemplary embodiments, the HLM 54 may alter a pump speed to either increase or decrease blood flow into or out of the blood reservoir 56. It may be important, for example, to prevent the blood level in the reservoir 56 from moving below a certain minimum level or volume. Accordingly, in various embodiments, the HLM will compare the blood level or volume to this minimum level and adjust pump speed appropriately.

According to other embodiments, the HLM may use the blood volume information for a variety of applications, including for example auto-regulation of pump occlusion, auto-loading of pump segments, conducting automatic occlusivity testing, performing automatic priming, automatic recirculating and debubbling, conducting automatic pressure tests, or performing automatic system emptying.

Figure 12:
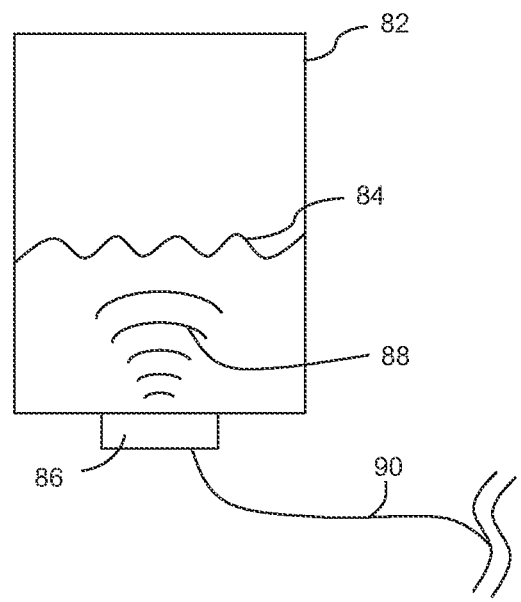
FIGS. 12-15 are illustrations blood reservoirs including a blood level sensor in accordance with various embodiments of the invention.
Figure 13:
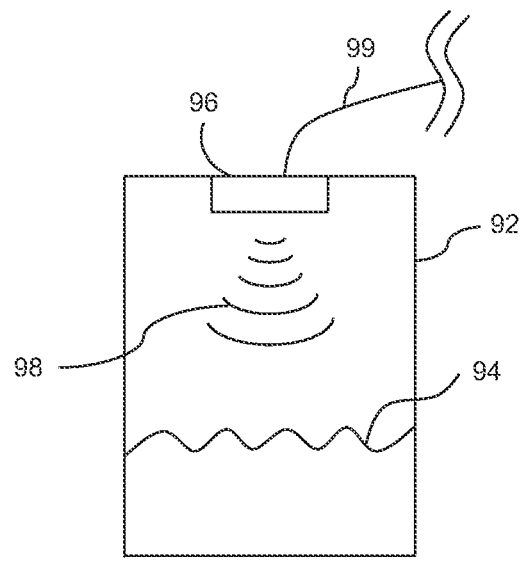

In some embodiments, the sensor may be an ultrasonic blood volume sensor, as illustrated in FIGS. 12 and 13. FIG. 12 is an illustration of a blood reservoir 82 that contains a volume of blood. The volume of blood defines an interface 84 between the volume of blood and the air or other fluid within the blood reservoir 82. In some embodiments, an ultrasonic transducer 86 that is located at or near a lower surface of the blood reservoir 82 can be used to locate the interface 84 by transmitting ultrasonic waves 88 through the fluid (e.g., blood) in the reservoir towards the interface 84. The reflectance of the ultrasonic waves 88 depends at least in part upon the fluid they are passing through. Thus, by measuring the reflectance, the ultrasonic transducer 86 can determine the distance from the interface 84 and thereby determine the fluid level. The ultrasonic transducer may be any of a variety of well-known and commercially available ultrasonic transducers. The ultrasonic transducer, may for example, by any of a variety of commercially available piezoelectric transducers or crystals. According to various exemplary embodiments, the ultrasound transducer is a piezoelectric transducer available from Piezo Technologies of Indianapolis, Ind., USA. In some embodiments, the ultrasonic transducer 160 may be an ultrasonic transducer such as the P43-F4V-2D-1C0-360E, the P41-D4V-2D-1C0-360E, and/or the P44-T4V-2D-001-180E ultrasonic transducers commercially available from Pil Sensoren GmbH in Erlensee, Germany.

In various embodiments, based on the fluid level and the known geometric configuration of the blood reservoir 82, a controller calculates the blood volume within the blood reservoir 82. In various embodiments, for example, the blood volume is calculated by integrating the detected blood level across the known cross sectional area at each location within the blood reservoir 82. In some embodiments, a cable 90 transmits a signal from the ultrasonic transducer 86 to the controller. In some embodiments, the information is transmitted wirelessly.

FIG. 13 is similar to FIG. 12, but shows a blood reservoir 92 having a blood volume defining an interface 94. In this embodiment, an ultrasonic transducer 96 is located at or near a top of the blood reservoir 92 and transmits ultrasonic waves 98 downward through the air above the fluid (e.g., blood) towards the interface 94. In these embodiments, the blood level in the reservoir is then calculated by subtracting the detected space between the top of the reservoir and the interface 94 from the known overall height of the reservoir. In some embodiments, a cable 99 transmits a signal from the ultrasonic transducer 96 while in other embodiments this is done wirelessly. A primary difference between the embodiments shown in FIGS. 12 and 13 is that in FIG. 12, the interface 84 is detected from below, or through the blood, while in FIG. 13 the interface 94 is detected from above.

In the various embodiments of FIGS. 12 and 13, the ultrasonic transducer 86, 96 may be either a structurally separate component adapted for coupling to the blood reservoir or the ultrasonic transducer 86, 96 may be structurally integrated into the blood reservoir. By way of example, the transducer may be a separate component which is adapted for coupling to the blood reservoir by an end user. Any of a variety of coupling techniques, including for example, adhesive, snap fit, interference fit, mechanical fasteners, and other known techniques may be employed by the end user to couple the ultrasonic transducer to either an upper surface (e.g., a lid) or a lower surface of the blood reservoir. In some embodiments, a hole or opening is formed in the blood reservoir, so that the ultrasonic transducer may communicate directly (i.e., without passing through a wall of the reservoir) with an interior chamber of the blood reservoir. By way of example, the ultrasonic transducer may also be structurally integrated into the blood reservoir by integrating the transducer during the molding process for forming the blood reservoir, including either a main body of the reservoir or a lid of the reservoir. In either case (i.e., structurally integrated or structurally separate), the end user must electrically couple the ultrasonic transducer to a controller or other device for receiving a signal from the transducer.

Figure 17:
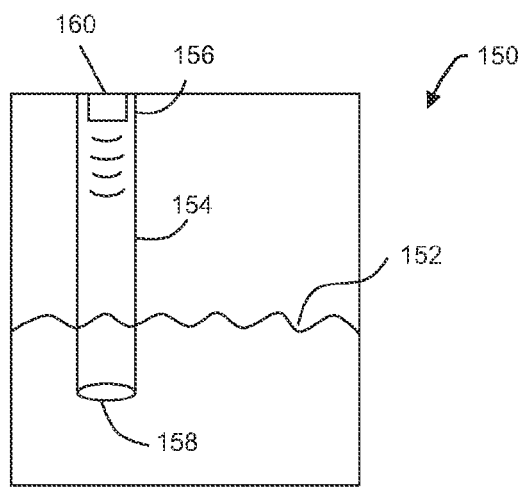
FIG. 17 is a schematic view of a blood reservoir including an ultrasonic sensor and a guide tube, according to exemplary embodiments of the invention.

In some embodiments, as shown for example in FIG. 17, an ultrasonic transducer such as the ultrasonic transducer 160 is disposed within or otherwise coupled to a structure that reduces potential interference or parasitic effects from other portions and components (e.g., blood filters) that may typically be located within the interior chamber of the blood reservoir. This configuration may help reduce the impact of internal components or reservoir wall condensation on the propagation of the ultrasonic wave, which in turn may improve the accuracy of the sensor measurements.

As shown in FIG. 17, a blood reservoir 150 has a blood volume defining an interface 152 between the volume of blood and the air or other fluid within the blood reservoir 150. A guide tube 154 having a top 156 and a bottom 158 extends downward into the volume of blood. According to various embodiments, the bottom 158 of the tube 154 is located between about 1 and about 25 mm from a bottom of the reservoir. According to some embodiments, the bottom 158 of the tube 154 is located between about 1 and about 10 mm from a bottom of the reservoir. An ultrasonic transducer 160 is disposed at or near the top 156 while the bottom 158 is open to the fluid within the blood reservoir 150. The ultrasonic transducer 160 is configured such that it generates ultrasonic waves directed generally along a longitudinal axis of the tube 154 toward the bottom of the reservoir (i.e., the blood contained within the reservoir). According to some embodiments, the top 156 of the guide tube 154 is located inside the reservoir at or near the lid or cover. According to other embodiments, the guide tube 154 passes through the lid or cover of the reservoir 150, such that the top 156 is located above or outside of the reservoir 150. In these embodiments, the transducer 160 may be attached or otherwise coupled to, at, or near the top 156 of the guide tube 154.

In various embodiments, the tube 154 includes openings and/or the top 156 of the tube is spaced from the top (e.g., lid or cover) of the blood reservoir to allow airflow into and out of the tube 154. According to exemplary embodiments, the tube 154 includes one or more holes in a wall of the tube near the top 156. According to various embodiments, these holes are sized with a diameter selected to reduce or eliminate the surface tension effect in the event blood reaches the hole. According to various embodiments, these holes are sized with a diameter selected to allow pressure equalization inside and outside of the tube, such that the blood level inside the tube is equal to or substantially equal to a blood level outside of the tube. According to some embodiments, the hole (or holes) is located at a location along the tube 154, which is inside the reservoir 150. According to other embodiments, the hole (or holes) is located at a location along the tube 154, which is outside the reservoir 150.

In some embodiments, the guide tube 154 may function as a waveguide for the ultrasonic waves. The ultrasonic waves emitted by the ultrasonic transducer 160 will propagate downward through the interior of the tube 154 and may not extend laterally outside the tube 154. The tube 154 may be dimensioned accordingly. In some embodiments, the tube 154 defines an interior chamber or lumen having an inner diameter of about 4 to about 16 millimeters. In one exemplary embodiment, the tube 154 has an outer diameter of about 16 millimeters and in inner diameter of between about 14 and about 15 mm. In some embodiments, the tube 154 may have any inner diameter sufficiently large to allow for the blood level inside the tube to be equal or substantially equal (e.g., within 0-5 percent) of the blood level in the reservoir outside of the tube. For example, in various embodiments, the inner diameter of the tube is selected so as to avoid or substantially eliminate any Venturi effect within the tube. In various embodiments, the tube 154 is disposed within the blood reservoir in a substantially vertical fashion (e.g., parallel or substantially parallel to the outer walls of the reservoir). In other embodiments, the tube 154 extends through the reservoir at some angle, for example at an angle of between 5 and 45 degrees, with respect to the vertical orientation.

In some embodiments, the guide tube 154 has an outer diameter of about 16 millimeters and in inner diameter of between about 14 and about 15 mm, and a vent hole diameter at or near the top 156 of the tube 154 of between about 1 and about 5 mm. According to some embodiments, the guide tube 154 as an inner diameter of about 10 mm and a vent hole having a diameter of about 5 mm, where the vent hole is located inside the reservoir.

In some embodiments, a blood volume may be calculated based upon a detected fluid level within the tube 154 that is extrapolated to the blood reservoir 150. By detecting the fluid level within the tube 154, rather than in the entire blood reservoir 150, improvements in accuracy may be obtained because potentially interfering elements and materials such as blood filters are excluded from the ultrasonic measurements.

According to various embodiments, a polyurethane sheet is disposed inside the tube 154. In these embodiments, in the event the blood level reaches the top of the reservoir, the polyurethane will prevent blood from contacting the piezoelectric transducer, which may not be separately sterilized. In these embodiments, the polyurethane is chosen with a thickness sufficiently small to allow the ultrasonic waves to pass therethrough.

In some embodiments, the blood volume sensor may be an infrared (IR) light sensor. In some embodiments, an infrared light source positioned at or near a lower surface of the blood reservoir 82 may be used to locate a fluid/air interface within the blood reservoir 82 by transmitting infrared light towards the interface. Alternatively, the infrared light sensor may be located above the interface. In some embodiments, the infrared light sensor may be located a short distance away from the blood reservoir 82 and thus can be attached to a mechanical holder for the blood level reservoir 82.

In some instances, the infrared light is reflected back towards the infrared light sensor. By measuring the reflectance, the location of the interface may be determined. In some embodiments, the infrared light travels through the blood to an infrared light sensor located opposite the infrared light sensor. By detecting changes in the received light, the interface location may be determined. By combining the interface location with known geometric parameters of the blood reservoir 82, the controller 20 can determine the blood volume within the blood reservoir 82. In some embodiments, this information is transmitted wirelessly to the controller 20.

Figure 14:
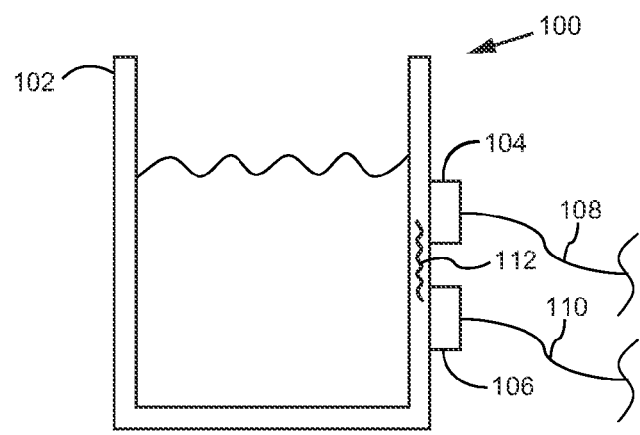

In some embodiments, as shown in FIG. 14, an ultrasonic blood volume sensor may include a pair of ultrasonic transducers (e.g., piezoelectric crystals). FIG. 14 shows a blood reservoir 100 that includes a side wall 102 containing a volume of blood. A first ultrasonic transducer 104 and a second ultrasonic transducer 106 are each secured to the side wall 102. In some embodiments, the first ultrasonic transducer 104 and/or the second ultrasonic transducer 106 may be a disposable ultrasonic transducer such as that described in U.S. Pat. No. 6,694,570 or U.S. Pat. No. 7,694,570, both of which are hereby incorporated by reference. In some embodiments, the first and second ultrasonic transducers 104, 106 may, for example, be adhesively secured to the side wall 102. In various embodiments, conductors 108 and 110 provide electrical communication between the first and second ultrasonic transducers 104, 106 and an unseen controller. In other embodiments, the first and second ultrasonic transducers 104, 106 may instead communicate wirelessly using any technique known in the art. In some embodiments, the controller may be similar to the controller 60 discussed previously with respect to the perfusion system 52.

In operation, the first ultrasonic transducer 104 produce a pulse of sonic energy that causes a flexural (e.g., elastic) wave 112 in the side wall 102, which then propogates or travels through the side wall 102. The second ultrasonic transducer 106 then receives the flexural wave 112. In this, designation of first and second, particularly as shown, is illustrative only.

It will be appreciated that the first and second ultrasonic transducers 104, 106 may be arranged in any desired arrangement with respect to one another. They are not required, for example, to be arranged with the first ultrasonic transducer 104 being vertically above the second ultrasonic transducer 106.

In some instances, the relative amount of liquid within the blood reservoir 100 may cause phase delays in the signal received by the second ultrasonic transducer 106. As there is a substantially linear relationship between the amount of the phase delay between the received components and the height of the blood level inside the reservoir 100, a controller may calculate a fluid level, or a change in the blood level, by analyzing the phase delay in the signal. According to some embodiments, the correlation between the phase delay and the level of blood in the reservoir 100 is determined experimentally by measuring the calculated phase delay at various blood levels. In some embodiments, for example, a phase delay is measured when the reservoir 100 is empty. As blood enters the reservoir 100, the speed of the flexural wave slows. In some embodiments, the decrease in speed may be correlated to a liquid level. According to various embodiments, the blood level in the reservoir 100 may be calculated using one or more of the techniques described in U.S. Pat. No. 6,631,639, which is hereby incorporated by reference in its entirety.

Figure 15:
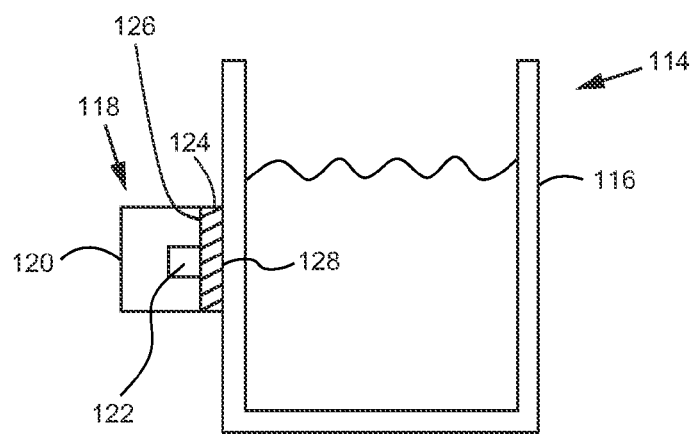

FIG. 15 shows an exemplary technique for attaching the ultrasonic transducers to the blood reservoir 114. As shown, an ultrasonic transducer 118 is releasably secured to the side wall 116. In some embodiments, the ultrasonic transducer 118 includes a housing 120 and a piezoelectric element 122 disposed within the housing 120. In some embodiments, the ultrasonic transducer 118 includes a section of double-sided tape 124. The tape 124 includes a first side 126 that is or can be adhesively secured to the housing 120 and a second side 128 that is or can be adhesively secured to the side wall 116 of the blood reservoir 114.

Figure 16:
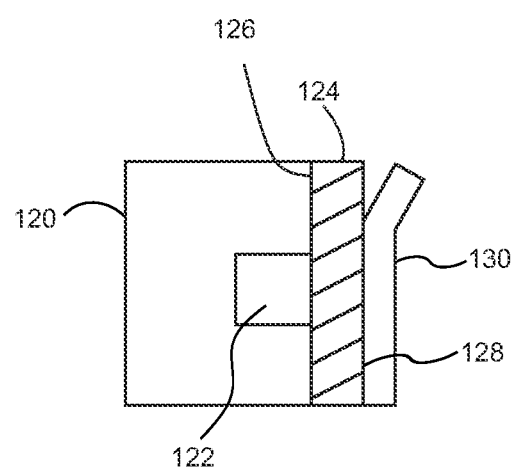
FIG. 16 is an illustration of the blood level sensor of FIG. 15.

FIG. 16 is an illustration of the ultrasonic transducer 118 free from the blood reservoir 114. In some embodiments, the ultrasonic transducer 118 may be marketed already attached to the blood reservoir 114. In some embodiments, the ultrasonic transducer 118 may be attachable at the point of use to any desired hard shell blood reservoir or soft shell reservoir. In some embodiments, a release liner 130 may be disposed on the second side 128 of the double face tape 124. The release liner 130 permits the ultrasonic transducer 118 to be handled yet can easily be removed in order to attach the ultrasonic transducer 118 to a blood reservoir. According to various embodiments, the ultrasonic transducer 118 is configured as described in U.S. Pat. No. 6,694,570 or U.S. Pat. No. 7,694,570.

While not illustrated, the ultrasonic transducer 118 may include one or more conductive wires that carry signals between the ultrasonic transducer 118 and a controller such as the controller 60 described above with respect to the perfusion system 52. In some embodiments, the ultrasonic transducer 118 may communicate wirelessly with the aforementioned controller.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The invention claimed is:

1. A perfusion system comprising:
a heart lung machine;
a blood reservoir adapted to hold a fluid, the blood reservoir having a capacity determined by a geometric configuration, wherein the blood reservoir includes an RFID tag that includes information describing the geometric configuration of the blood reservoir;
an ultrasonic sensor coupled to the blood reservoir and configured to determine a fluid level within the blood reservoir; and
a controller coupled to the heart lung machine;
an RFID receiver coupled to the controller, the RFID receiver configured to communicate with the RFID tag and receive from the RFID tag information describing the geometric configuration of the blood reservoir, the controller configured to receive the fluid level from the ultrasonic sensor and to receive the information describing the geometric configuration of the blood reservoir from the RFID receiver, the controller configured to calculate a blood volume contained within the blood reservoir based on the fluid level and the geometric configuration;
a display coupled to the heart lung machine, the display configured to display the calculated blood volume;
wherein the heart lung machine is configured to adjust an operating parameter based on the calculated blood volume.

2. The perfusion system of claim 1, wherein the ultrasonic sensor comprises a spaced apart pair of ultrasonic transducers coupled to a wall of the blood reservoir.

3. The perfusion system of claim 2, wherein the pair of ultrasonic transducers comprises a first ultrasonic transducer configured to emit a single pulse that generates a flexural wave in the wall and a second ultrasonic transducer configured to receive the flexural wave.

4. The perfusion system of claim 3, wherein the controller is configured to determine the fluid level within the blood reservoir based on phase delays in the flexural wave.

5. The perfusion system of claim 1, wherein the ultrasonic sensor comprises a piezoelectric element disposed within a housing.

6. The perfusion system of claim 5, wherein the ultrasonic sensor is removably secured to the blood reservoir.

7. The perfusion system of claim 6, wherein the ultrasonic sensor may be adhesively secured to the blood reservoir.

8. The perfusion system of claim 7, wherein the ultrasonic sensor further comprises double faced tape, with one adhesive side secured to the housing and an opposing adhesive side secured to the blood reservoir.

9. The perfusion system of claim 1, wherein the ultrasonic sensor is molded into a wall of the blood reservoir.

10. The perfusion system of claim 1, wherein the controller is further configured to operate the heart lung machine in accordance with the calculated blood volume in the blood reservoir.

11. The perfusion system of claim 1, further comprising a polymeric tube disposed within the blood reservoir, with the ultrasonic sensor disposed proximate an upper end of the polymeric tube.

12. A blood reservoir system comprising:
a blood reservoir configured to hold a blood volume,
an ultrasonic sensor securable to the blood reservoir, the ultrasonic sensor configured to provide an electrical signal indicative of a blood level within the blood reservoir;
an RFID tag securable to the blood reservoir, the RFID tag configured to provide information describing the geometric configuration of the blood reservoir; and
a controller configured to receive the electrical signal from the ultrasonic sensor indicative of the blood level within the blood reservoir and to receive from the RFID tag the information describing the geometric configuration of the blood reservoir, the controller configured to calculate and output a signal indicative of a blood volume within the blood reservoir.

13. The blood reservoir system of claim 12, wherein the ultrasonic sensor is structurally integrated into the blood reservoir.

14. The blood reservoir system of claim 13, wherein the ultrasonic sensor is integrated into a cover portion of the blood reservoir.

15. The blood reservoir system of claim 12, wherein the ultrasonic sensor is structurally separate from the blood reservoir and further wherein the ultrasonic sensor is configured for removably coupling with the blood reservoir.

16. The blood reservoir system of claim 12, further comprising a guide tube disposed within the blood reservoir and coupled to a top surface of the reservoir and further wherein the ultrasonic sensor is secured to the reservoir such that the sensor is in communication with an interior lumen of the guide tube.

17. The blood reservoir system of claim 12, wherein the blood reservoir comprises a soft shell reservoir.

18. The blood reservoir system of claim 12, wherein the blood reservoir comprises a hard shell reservoir.

* * * * *